United States Patent [19]

Ohmori et al.

[11] Patent Number: 5,274,177

[45] Date of Patent: Dec. 28, 1993

[54] GLUTATHIONE-S-LOWER FATTY ACID DERIVATIVE

[75] Inventors: Shinji Ohmori, Okayama; Kazumi Ogata, Toyonaka; Takahiro Sakaue, Itami, all of Japan

[73] Assignee: Senju Pharmaceutical Co., Ltd., Osaka, Japan

[21] Appl. No.: 773,595

[22] PCT Filed: Apr. 26, 1991

[86] PCT No.: PCT/JP91/00581

§ 371 Date: Dec. 13, 1991

§ 102(e) Date: Dec. 13, 1991

[87] PCT Pub. No.: WO91/16338

PCT Pub. Date: Oct. 31, 1991

[30] Foreign Application Priority Data

Apr. 26, 1990 [JP] Japan .................. 2-112260

[51] Int. Cl.$^5$ .......................... C07C 323/25
[52] U.S. Cl. ...................... 560/153; 530/331; 562/556; 562/557
[58] Field of Search ............... 560/153; 562/556, 557; 530/331

[56] References Cited

FOREIGN PATENT DOCUMENTS 60-123497  7/1985  Japan .
60-237963  11/1985  Japan .
61-249958  11/1986  Japan .
2-500841   3/1990  Japan .

OTHER PUBLICATIONS

*Anal. Biochem.*, vol. 183, No. 1, Deterding et al, pp. 94–107, (1989).
*Br. J. Ind. Med.*, vol. 32, No. 1, Edwards, pp. 31–38, (1975).
*Biochem. J.*, vol. 125, No. 1, Speir et al., pp. 267–273, (1971).
*Chemical Abstracts*, vol. 56, No. 1, Entry No. 716f, Jan. 8, 1962.

*Primary Examiner*—José G. Dees
*Assistant Examiner*—Vera C. Clarke
*Attorney, Agent, or Firm*—Wenderoth, Lind & Ponack

[57] ABSTRACT

This invention relates to a glutathione-S-lower fatty acid derivative of the formula $$\text{HOOC}-\underset{\underset{NH_2}{|}}{\text{CH}}-\text{CH}_2\text{CH}_2\text{CO}-\text{NH}-\underset{\underset{\underset{\underset{R_2\ R_3}{|\ |}}{CH_2-S+CH\frac{}{n}CH-COR_4}}{|}}{\text{CH}}-\text{CO}-\text{NHCH}_2\text{COOR}_1$$

[wherein $R_1$ is a lower alkyl group which may be substituted; $R_2$ is a hydrogen atom; $R_3$ is a hydrogen atom or a lower alkyl group which may be substituted; $R_4$ is a hydroxyl group, a lower alkoxy group which may be substituted; n means 1] or a salt thereof, and a method for production thereof.

The glutathione-S-lower fatty acid derivative of the present invention or a salt thereof shows an excellent antihepatopathic activity and can be used with advantage as a drug for the treatment of various hepatic disorders.

3 Claims, No Drawings

GLUTATHIONE-S-LOWER FATTY ACID DERIVATIVE

TECHNICAL FIELD

The present invention relates to a novel and useful glutathione-S-lower fatty acid derivative and a method for production thereof.

BACKGROUND ART

There are known several glutathione-S-lower fatty acid derivatives. Among them, S-(2-carboxypropyl)-glutathione has been isolated from onion and garlic (Virtanen and Matikkala, 1960; Suzuki et al, 1961) but there is little information on its pharmacologic activity.

The inventors of the present invention previously found that glutathione-S-succinic acid derivatives have platelet aggregation-inhibitory, antiinflammatory, anti-allergic, antitumoral and hepatic impairment-protective activities (Japanese Kokai Patent Application No. 63-8337 and Japanese Patent Application No. 1-79956, No. 1-183484, No. 1-251534, No. 1-256370 and No. 2-36745).

In search of still more pharmacologically active compounds, the inventors of the present invention synthesized a variety of novel glutathione derivatives and screened them, as well as said S-(2-carboxypropyl)-glutathione, for their pharmacologic activities. As a consequence, they found that S-(2-carboxypropyl)-glutathione and a series of compounds which can be synthesized by reacting glutathione or an ester thereof with an $\alpha, \beta$-unsaturated fatty acid, such as acrylic acid, methacrylic acid, crotonic acid, cinnamic acid, etc., or an $\alpha$ (or $\beta$)-halogenated organic monocarboxylic acid, such as monochloroacetic acid, or an ester or amide thereof have excellent antihepatopathic efficacy. The present invention has been attained based on this finding.

DISCLOSURE OF THE INVENTION

The present invention relates to
1) a compound of the formula $$\text{HOOC}-\underset{\underset{\text{NH}_2}{|}}{\text{CH}}-\text{CH}_2\text{CH}_2\text{CO}-\text{NH}-\underset{\underset{\text{CH}_2-\text{S}-(\text{CH})_{\overline{n}}-\underset{\underset{R_3}{|}}{\text{CH}}-\text{COR}_4}{|}}{\text{CH}}-\text{CO}-\text{NHCH}_2\text{COOR}_1 \quad [\text{I}]$$

[wherein $R_1$ is a lower alkyl group which may be substituted; $R_2$ is a hydrogen atom; $R_3$ is a hydrogen atom or a lower alkyl group which may be substituted; $R_4$ is a hydroxyl group or a lower alkoxy group which may be substituted; n means 1] or a salt thereof; and, 2) a method for production thereof.

As the lower alkyl of $R_1$, and where $R_3$ in the above formula [I] means a lower alkyl group, such alkyl group preferably has 1 to 10 carbon atoms. This alkyl group may be straight-chain, branched or cyclic or contain a cyclic moiety. Thus, methyl, ethyl, n-propyl, isopropyl, cyclopropyl, n-butyl, tert-butyl, sec-butyl, n-pentyl, 1-ethylpropyl, isopentyl and benzyl may be mentioned by way of example.

Referring, further, to the above formula, where n is equal to 1 and $R_2$ is a hydrogen atom.

Further in the formula, when $R_4$ is a lower alkoxy group, the lower alkoxy group includes, among others, methoxy, ethoxy, propoxy, isopropoxy, n-butoxy, isobutoxy, sec-butoxy, tert-butoxy, n-pentyloxy, isopentyloxy, tert-pentyloxy, neopentyloxy, 2-methylbutoxy, 1,2-dimethylpropoxy, 1-ethylpropoxy and so on. The lower alkoxy group may have a hydroxyl group or a cyclic group such as phenyl.

The above compound can occur as the free acid or as a pharmaceutically acceptable salt thereof, for instance an alkali metal salt thereof, e.g. the sodium salt, potassium salt, etc., or an alkaline earth metal salt, e.g. the calcium salt, magnesium salt and so on. Regarding the salt, any or all of the carboxyl functions available in the compound may have been converted to such salt or salts. Any of these salts can be used advantageously in the manufacture of the antihepatopathic composition of the present invention.

The compound of the present invention can be chemically synthesized as follows. The present compound is obtainable by reacting glutathione or an ester thereof with an organic monocarboxylic acid represented by the formula or an ester thereof:

$$R_2-A-COOH \quad [\text{II}]$$

[wherein $R_2$ is a hydrogen atom; the symbol A is a bivalent group represented by the formula $$-\underset{\underset{R_3}{|}}{\text{CH}}=\text{C}-$$

(wherein $R_3$ is a hydrogen atom or a lower alkyl group which may be substituted with a group which does not react with SH group) or the formula $$-\underset{\underset{X}{|}}{\text{CH}}-\underset{\underset{R_3}{|}}{\text{CH}}-$$

(wherein X is a halogen atom and $R_3$ is the same as previously defined)] and if necessary further esterifying the resulting compound. As the compounds represented by formula [II] are exemplified $\alpha, \beta$-unsaturated fatty acid, such as acrylic acid and methacrylic acid, $\beta$-halogenated organic monocarboxylic acid, such as $\beta$-chloroproponic acid. More specifically, either glutathione or a glutathione monoester ($\gamma$-glutamylcysteinylglycine ester) which is obtainable by reacting glutathione with the corresponding alcohol in the presence of an acid, e.g. sulfuric acid, is reacted in water or aqueous medium with an $\alpha, \beta$-unsaturated acid, e.g. acrylic acid, methacrylic acid, etc., or an $\beta$-halogenated organic monocarboxylic acid, e.g. $\beta$-chloropropionic acid, or an ester or amide thereof, preferably at pH about 4 to 8, at room temperature or under mild heating with stirring. This reaction readily goes to completion. This reaction mixture is purified by column chromatography or recrystallization from a solvent to give the object compound.

Since most of the compounds synthesized as above have asymmetric carbon within the molecule, they may occur as optical isomers but all such optically active compounds as well as mixtures thereof can be used for purposes of the present invention.

The antihepatopathic composition comprising the compound of present invention effectively inhibits the onset of acute and chronic hepatic disorders, suppresses elevation of GOT and GPT values and, as such, is not only useful for the prevention and treatment of acute or chronic hepatitis but also effective in the prevention and treatment of hepatocirrhosis. It can also be used with advantage in cases of hepatic impairment induced by drugs such as acetaminophen.

The antihepatopathic composition comprising the compound of the present invention can be administered orally or parenterally. With regard to dosage form, it can be provided, for example, in various solid dosage forms such as tablets, granules, powders, capsules, etc. or in liquid dosage forms such as injectable preparations. These preparations can be manufactured by the established pharmaceutical procedures and according to the type of disease to be controlled. In such preparations, there may be incorporated conventional additives such as the binder, disintergrating agent, thickener, dispersing agent, reabsorption promoter, corrigent, buffer, surfactant, cosolvent, preservative, emulsifier, isotonizing agent, stabilizer, pH adjusting agent and so on.

The dosage of the active ingredient according to the present invention is dependent on the particular species of compound used, type of disease, patient's age and body weight, dosage form, indication and so on. In the case of an injectable preparation, for instance, about 1 to 500 mg per day per adult is administered once a day, and in the case of an oral preparation, about 10 to 2000 mg per dose per adult is administered a few times a day.

Depending on the objective and necessity of treatment, the antihepatopathic composition comprising the compound of the present invention may contain two or more species of the active compounds in suitable proportions.

Unless contrary to the object of the invention, the antihepatopathic composition comprising the compound of the present invention may additionally contain other active ingredients having similar efficacy or different efficacies in suitable proportions.

BEST MODES OF WORKING THE INVENTION

The following synthesis examples, test example and preparation examples are intended to illustrate the invention in further detail.

SYNTHESIS EXAMPLE 1

S-(2-Methyl-2-carbethoxyethyl)glutathione isopropyl ester [$R_1=C_3H_7$, $R_2=H$, $R_3=CH_3$, $R_4=OC_2H_5$, $n=1$]

In 50 ml of water is suspended 4.0 g of glutathione isopropyl ester sulfate and the solution is adjusted to pH 6.5 with 2N-sodium hydroxide. After 2 ml of ethyl methacrylate is added, the mixture is stirred at room temperature for 3 hours and concentrated. To the residue is added ethanol and the precipitated inorganic salt is filtered off. To the filtrate is added acetone and the resulting crop of colloidal crystals is recovered by filtration and purified by Sephadex G-10 column chromatography (eluent: water-ethanol=1:1). Recrystallization from ethanol-acetone gives 2.4 g of amorphous crystals. TLC, silica gel Rf=0.48 (n-butanol-acetic acid-water=4:1:1)

Elemental analysis, for $C_{19}H_{33}O_8N_3S$: Calcd. (%): C, 49.23; H, 7.18; N, 9.06. Found (%): C, 49.09; H, 7.10; N, 9.16.

SYNTHESIS EXAMPLE 2

S-(2-Methyl-2-carboisobutoxyethyl)glutathione isopropyl ester [$R_1=C_3H_7$, $R_2=H$, $R_3=CH_3$, $R_4=OC_4H_9$, $n=1$]

Using 4.0 g of glutathione isopropyl ester sulfate and 1.6 g of isobutyl methacrylate, the procedure of Synthesis Example 1 is followed (stirring time: 48 hours). The resulting crop of crystals is recrystallized from ethanol-ethyl acetate-petroleum benzin to give 2.0 g of colorless amorphous crystals. TLC, silica gel Rf=0.54 (n-butanol-acetic acid-water=4:1:1)

Elemental analysis, for $C_{21}H_{37}O_8N_3S$: Calcd. (%): C, 51.31; H, 7.59; N, 8.55. Found (%): C, 51.13; H, 7.48; N, 8.57.

TEST EXAMPLE 1

Effect on acetaminophen-induced hepatic impairment

Method: Male SD rats (body weights ca. 180 g) purchased from Japan SLC were used. The test substance was orally administered (0.5 mmole/kg) and one hour later 300 mg/kg of acetaminophen was intraperitoneally administered. After 24 hours, blood was drawn from the abdominal aorta and the serum was separated. Using this serum, s-GOT and GPT were determined.

Result: Two different glutathione derivatives were tested for inhibitory effect on acetaminophen-induced hepatic impairment. As shown in Table 1, compound Nos. 1 and 2 (corresponding to the structures indicated in the table) showed significant antihepatopathic effects.

TABLE 1

| No. | Test substance | s-GOT | s-GPT |
|---|---|---|---|
| — | Physiological saline (control) | 5269 ± 835 | 2060 ± 494 |
| 1 | $R_1 = C_3H_7$<br>$R_2 = H$<br>$R_3 = CH_3$<br>$R_4 = OC_2H_5$<br>$n = 1$ | 1570 ± 511[*2] (70.2) | 529 ± 168[*1] (74.3) |
| 2 | $R_1 = C_3H_7$<br>$R_2 = H$<br>$R_3 = CH_3$<br>$R_4 = OC_4H_9$<br>$n = 1$ | 163 ± 89[*3] (96.9) | 52 ± 29[*2] (97.5) |

The unit: IU/l; each value represents the mean ± S.E. n = 7–10; the figure in parenthesis represents (%) inhibition.
Significance difference from physiological saline:
[*1]$p < 0.05$, [*2]$p < 0.01$, [*3]$p < 0.001$.

PREPARATION EXAMPLE 1

Oral Tablet

S-(2-Methyl-2-carboisobutoxyethyl)glutathione isopropyl ester

| | |
|---|---|
| isopropyl ester | 100 mg |
| Lactose | 80 mg |
| Starch | 17 mg |
| Magnesium stearate | 3 mg |

Using the above materials per tablet, tablets for oral administration were manufactured by the established pharmaceutical procedure. Where necessary, the tablets may be sugar-coated.

We claim:
1. A compound of the formula

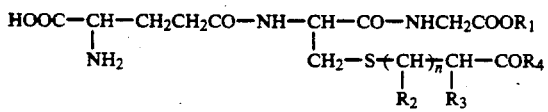

wherein $R_1$ is lower alkyl, $R_2$ is hydrogen, $R_3$ is lower alkyl, $R_4$ is hydroxy or lower alkoxy, and n is 1, or a pharmaceutically acceptable salt thereof.

2. A compound according to claim 1 wherein the compound is S-(2-methyl-2-carbethoxyethyl)glutathione isopropyl ester.

3. A compound according to claim 1 wherein the compound is S-(2-methyl-2-carboisobutoxyethyl)-glutathione isopropyl ester.

* * * * *